United States Patent [19]

Kon et al.

[11] Patent Number: 5,399,691
[45] Date of Patent: Mar. 21, 1995

[54] SUBSTITUTED BENZOYLUREA DERIVATIVES OR THEIR SALTS

[75] Inventors: Kenji Kon, Ohtsu; Hiroshi Okada, Kusatsu, both of Japan

[73] Assignee: Ishihara Sangyo Kaisha Ltd., Osaka, Japan

[21] Appl. No.: 986,488

[22] Filed: Dec. 7, 1992

[30] Foreign Application Priority Data

Dec. 5, 1991 [JP] Japan ............................ 3-360431

[51] Int. Cl.⁶ .......................................... C07D 239/34
[52] U.S. Cl. ......................................... 544/316; 544/123
[58] Field of Search ............................... 544/316, 123

[56] References Cited

FOREIGN PATENT DOCUMENTS 0413977 2/1991 European Pat. Off. .

*Primary Examiner*—John M. Ford
*Attorney, Agent, or Firm*—Oblon, Spivak, McClelland, Maier & Neustadt

[57] ABSTRACT

The present invention provides a substituted benzoylurea derivative having the formula (I),

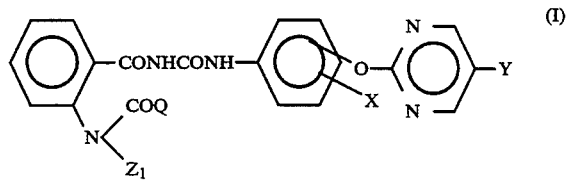

(wherein Q is a $-R_1N(Z_2)Z_3$ group or a $-R_2N(Z_4)COR_1N(Z_2)Z_3$ group, $R_1$ and $R_2$ are respectively an alkanediyl group which may be substituted with a lower alkylthio group or a phenyl group, $Z_1$, $Z_2$, $Z_3$ and $Z_4$ are respectively a hydrogen atom or a lower alkyl group, $R_1$ and $Z_2$ may be bonded with each other to form a heterocyclic ring with an adjacent nitrogen atom, X is a halogen atom, a lower alkyl group or a $CF_3$ group, and Y is a halogen atom) or its salt, effective as an antitumor agent; a method for producing the same; an antitumor composition containing the same; and an intermediate product for producing the same.

6 Claims, No Drawings

SUBSTITUTED BENZOYLUREA DERIVATIVES OR THEIR SALTS

The present invention relates to a novel antitumor composition containing a substituted benzoylurea derivative or it salts.

Heretofore, various types of a benzoylurea type compound have been proposed as an active ingredient for an antitumor composition. For example, European Patent Publication No. 413977 discloses a benzoylurea type compound having a substituted or non-substituted amino group at the 2-position of the benzoyl group.

However, the fat-solubility of this compound has been improved, but its water-solubility is low and a compound having a high water-solubility is demanded as mentioned below.

A benzoylurea type compound is inherently poor in solubility to water or an organic solvent. In order to develop a benzoylurea type compound as an antitumor composition, it is necessary to improve its solubility.

The present invention provides a novel substituted benzoylurea derivative having an improved water-solubility or its salt, a method for producing the same, an antitumor composition containing the same and an intermediate product for producing the same.

The present inventors have paid their attention to the high antitumor activity of a benzoylurea type compound having an amino group at the 2-position of the benzoyl group disclosed in the above European Patent Publication No. 413977, and have studied to find a benzoylurea type derivative having an improved water-solubility while maintaining the high antitumor activity. As this result, they have found that a desired compound can be obtained by introducing a specific aminoacyl group into the amino group at the 2-position of the benzoyl group of said benzoylurea type compound, and have completed the present invention.

Thus, the present invention relates to a substituted benzoylurea derivative having the formula (I),

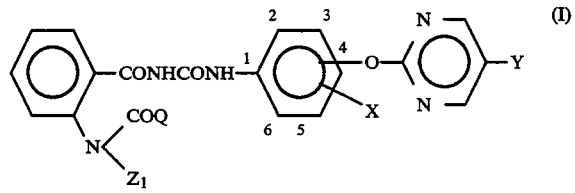

(wherein Q is a $-R_1N(Z_2)Z_3$ group or a $-R_2N(Z_4)COR_1N(Z_2)Z_3$ group, $R_1$ and $R_2$ are respectively an alkanediyl group which may be substituted with a lower alkylthio group or a phenyl group, $Z_1$, $Z_2$, $Z_3$ and $Z_4$ are respectively a hydrogen atom or a lower alkyl group, $R_1$ and $Z_2$ may be bonded with each other to form a heterocyclic ring with an adjacent nitrogen atom, X is a halogen atom, a lower alkyl group or a trifluoromethyl group, and Y is a halogen atom) or its salt, a method for producing the same, an antitumor composition containing the same and an intermediate product for producing the same.

In the formula (I), the alkanediyl group of $R_1$ or $R_2$ contained in the subtituent Q may be either of a straight chained or branched chained group having a carbon number of from 1 to 8, examples of which include a methylene group, an ethylene group, a 1,1-ethanediyl group, a propylene group, a 1,1- or 1,2-propanediy group, a butylene group, a 1,1-, 1,2- or 1,3-butanediyl group, a pentylene group, or a 1,1-, 1,2-, 1,3- or 1,4-pentanediyl group. Also, these alkanediyl groups may be subsitutued with a lower alkylthio group or a phenyl group. The lower alkyl moiety of a lower alkylthio group as a substituent defined by $R_1$ or $R_2$, a lower alkyl group defined by $Z_1$, $Z_2$, $Z_3$ or $Z_4$, or a lower alkyl group defined by a sutstitutent X, may be either of a straight chained or branched chained group having a carbon number of from 1 to 6, preferably from 1 to 2, examples of which include a methyl group, an ethyl group, an n-propyl group, an isopropyl group, an n-butyl group, an isobutyl group, a tert-butyl group or a pentyl group. $R_1$ and $Z_2$ may be bonded with each other to form a heterocyclic ring with an adjacent nitrogen atom. Examples of the heterocyclic ring include a morpholino group, an aziridinyl group, a pyrrolidinyl group, a piperidino group or a pyrrolyl group. Examples of a halogen atom defined by a substituent X or Y include a fluorine atom, a chlorine atom, a bromine atom or an iodine atom.

The substituted benzoylurea derivative of the formula (I) forms a salt with the amino moiety contained in a substitutent Q. As the salt of the substituted benzoylurea derivative used as an antitumor agent may be any type of salts so long as they are pharmaceutically acceptable, examples of which include salts formed by inorganic acids such as hydrochloric acid, hydrobromic acid, sulfuric acid, phosphoric acid or nitric acid; or organic acids such as acetic acid, methanesulfonic acid, oxalic acid, tartaric acid, succinic acid, maleic acid, fumaric acid, adipic acid, gluconic acid, lactic acid, citric acid, malic acid, ascorbic acid, benzoic acid, salicylic acid, tannic acid, pamoic acid, alginic acid, naphthalenesulfonic acid, naphthalenedisulfonic acid or polygalacturonic acid. Among them, salts of hydrochloric acid, hydrobromic acid, sulfuric acid, phosphoric acid, nitric acid, methanesulfonic acid, tartaric acid, maleic acid, lactic acid or citric acid are preferable. Also, a salt may be formed with an alkylhalide. Such a salt may also be included as the salt of the substituted benzoylurea derivative of the present invention.

Compounds represented by the formula (I) include an optical isomer derived from an asymmetric carbon contained in a substitutent Q. The substituted benzoyl-urea derivatives of the present invention include D-form, L-form and racemate.

Preferable examples of the compound of the present invention include substituted benzoylurea derivatives represented by the formula (I) or their salts, wherein (1) $Z_1$ is a hydrogen atom, (2) Q is a $-R_1N(Z_2)Z_3$ group, $R_1$ is an alkanediyl group, and $Z_2$ and $Z_3$ are respectively a hydrogen atom or a lower alkyl group, (3) X is a chlorine atom or a methyl group, and Y is a chlorine atom or a bromine atom, and (4) the substituted pyrimidinyloxy group is at the 4-position and X is at the 3-position of the phenyl group to the urea bond in the formula (I).

More preferable examples include N-[4-(5-bromo-2-pyrimidinyloxy)-3-methylphenyl]-N'-(2-glycylamino)-benzoylurea; N-[4-(5-bromo-2-pyrimidinyloxy)-3-methylphenyl]-N'-[2-(N,N-dimethylglycyl)amino]benzoylurea; N-[4-(5-bromo-2-pyrimidinyloxy)-3-methylphenyl]-N'-(2-sarcosylamino)benzoylurea; or their salts.

The substituted benzoylurea derivative of the formula (I) can be prepared by the following method.

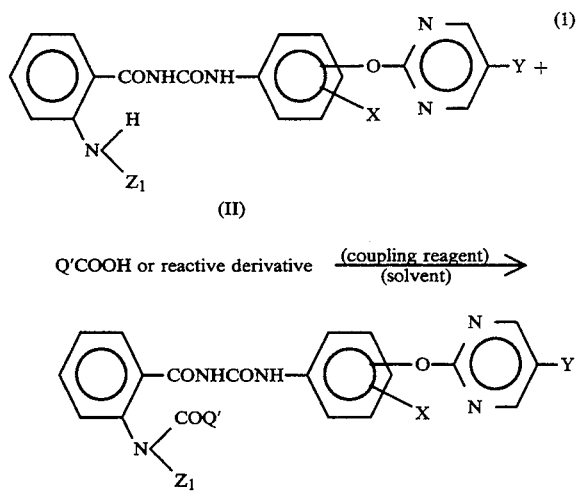

(wherein Q' is a —R₁N(Z₂)A group or a —R₂N(Z₄)COR₁N(Z₂)A group, A is a protecting group or a lower alkyl group, and X, Y, R₁, R₂, Z₁, Z₂ and Z₄ are as defined above, provided that A is a protective group when Z₂ is a hydrogen atom.)

When A contained in Q' is a protective group, the protecting group is removed after the above reaction.

(2) The substituted benzoylurea derivative of the formula (I) or its salt obtained in the above step (1), is converted into a pharmaceutically acceptable salt.

The same reaction as generally known peptide synthesis (see "Peptide Gosei no Kiso to Jikken (Basic paptide synthesis and experiment") written by N. Izumiya, T. Kato, H. Aoyagi and M. Waki and published by Maruzen Kabushiki Kaisha) can be used for the reaction of the above step (1). For example, there are enumerated C-terminal activation method, coupling reagent method and the like. In any of the methods, the compound of the formula Q'COOH or its reactive derivative of the formula Q'COB is used as the reaction starting material, and the reaction starting material can be used in accordance with the above mentioned peptide systhesis. The C-terminal activation method 6an be further classified into active esterification method, mixed acid anhydride method, azide method and the like. In the active esterification method, B is a 4-nitrophenyloxy group, a 1,3,5-trichlorophenyloxy group, a pentafluorophenyloxy group, a succinimideoxy group, a 5-norbornene-2,3-dicarboximideoxy group, a 8-quinolyloxy group or the like. In the mixed acid anhydride method, B is an isobutyloxycarbonyloxy group, a pivaloyloxy group or the like. In the azide method, B is an azide group. In the C-terminal activation method, a base and a solvent may optionally be used. The coupling reagent method can be further classified into carbodiimide method, carbodiimide-additive method, carbonyldiimidazol method, Woodward's reagent K method, N-ethyl-2'-hydroxybenzisoxazolium fluoroborate method, 1-ethoxycarbonyl-2-ethoxy-1,2-dihydroxyquinoline method, Bop reagent method, diphenylphosphoryl azide method or the like. In the coupling reagent method, B is a hydroxy group. In the coupling reagent method, a base and a solvent may optionally be used.

In the above step (1), when A is a protective group, the compound is represented by the following formula (III) and generally known examples of the protective group include a benzyloxycarbonyl group, a tert-butyloxycarbonyl (hereinafter referred to as "Boc") group, a p-biphenylisopropyloxycarbonyl group, a formyl group, a 2-nitrophenylsulphenyl group, a diphenylphosphinothioyl group and the like.

A lower alkyl group defined by A contained in Q' is the same as those defined by Z₃.

A generally known method can be employed as a method for removing the protective group, examples of which include a catalytically reducing method, a method of using an acid such as hydrochloric acid or trifluoroacetic acid, and the like. Depending on the type of the protective group, an appropriate method for removing the protective group may be employed. When an acid is used in the method for removing the protective group, the substituted benzoylurea detivative of the formula (I) is obtained as a salt of the acid used.

The salts of the substituted benzoylurea derivatives of the formula (I) in the above step (2), may include a salt other than a pharmaceutically acceptable salt obtained in the above step (1).

In the above step (1), a substituted benzoylurea type compound of the formula (II) is described in European Patent Publication No. 413977, and can be prepared in accordance with the method disclosed therein. Also, the substututed benzoylurea type compound of the formula (II) wherein Z₁ is a hydrogen atom, can be prepared by reducing a compound of the formula (IV)

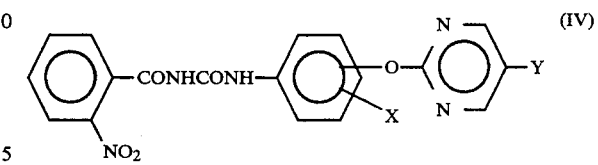

(wherein X and Y are as defined above) with sodium hydrosulfite in the presence of water and a solvent such as dimethylformamide.

Now, the present invention is further illustrated by the following examples, but should not be limited thereto.

EXAMPLES

Preparation Example 1

Preparation of N-[4-(5-bromo-2-pyrimidinyloxy)-3-chlorophenyl]-N'-[2-(N,N-dimethylglycyl)amino]benzoylurea hydrochloride (1) 7.06 g of 4-dimethylaminopyridine was added to 900 ml of dry methylene chloride, and 11.0 g of 1-ethyl-3-(3-dimethylaminopropyl)carbodiimide hydrochloride and 23.7 g of N-(2-aminobenzoyl)-N'-[4-(5-bromo-2-pyrimidinyloxy)-3-chlorophenyl]urea were added thereto in order. After stirring the reaction mixture at room temperature for 15 minutes, 5.94 g of N,N-dimethylglycine was added thereto, and the mixture was stirred at room temperature for 40 hours. Insoluble fractions were removed by filtration, and was washed with methylene chloride. The filtrate was concentrated, and the residue was purified by silica gel column chromatography (developing solvent: methylene chloride/n-hexane/ethyl acetate=1/1/1) to obtain 2.86 g of N-[4-(5-bromo-2-pyrimidinyloxy)-3-chlorophenyl]-N'-[2-(N,N-dimethylglycyl)amino]benzoylurea having a melting point of 192°–193° C.

(2) 0.5 g of the above prepared N-[4-(5-bromo-2-pyrimidinyloxy)-3-chlorophenyl]-N'-[2-(N,N-dimethylglycyl)amino]benzoylurea was dissolved in 2 ml of N,N-dimethylformamide and 10 ml of methylene chloride, and hydrochloric acid gas was introduced to the mixture under cooling with ice. Thereafter, the reaction mixture was allowed to stand at room temperature for 2 hours, and methylene chloride was distilled off. Diethylether was then added to precipitate a crystal, and the crystal was collected by filtration. The crystal thus obtained was dried in vacuo to obtain 0.42 g of the aimed product having a melting point of 164°–169° C. (the following compound No. 2).

Preparation Example 2

Preparation of N-[4-(5-bromo-2-pyrimidinyloxy)-3-chlorophenyl]-N'-(2-glycylamino)benzoylurea hydrochloride (1) 5.80 g of 4-dimethylaminopyridine was added to 1,000 ml of dry methylene chloride, and 9.11 g of 1-ethyl-3-(3-dimethylaminopropyl)carbodiimide hydrochloride and 20.0 g of N-(2-aminobenzoyl)-N'-[4-(5-bromo-2-pyrimidinyloxy)-3-chlorophenyl]urea were added thereto in order. After stirring the reaction mixture at room temperature for 15 minutes, 8.33 g of Boc-glycine was added thereto, and the mixture was stirred at room temperature for 40 hours. Thereafter, insoluble fractions were removed by filtration and washed with methylene chloride. After concentrating the filtrate, the residue was purified by silica gel column chromatography (developing solvent: methylene chloride/ethyl acetate=9/1) to obtain 3.5 g of N-[4-(5-bromo-2-pyrimidinyloxy)-3-chlorophenyl]-N'-(2-Boc-glycylamino)benzoylurea having a melting point of 145°–192° C.

(2) 5.08 g of N-[4-(5-bromo-2-pyrimidinyloxy)-3-chlorophenyl]-N'-(2-Boc-glycylamino)benzoylurea obtained in the same manner as the above reaction was reacted with 48 ml of trifluoroacetic acid at room temperature for 1.5 hours with stirring. After completing the reaction, an excess amount of trifluoroacetic acid was distilled off under reduced pressure, and diethylether was added to the residue. After stirring the mixture for 1 hour, a crystal thus precipitated was collected by filtration to obtain 3.35 g of N-[4-(5-bromo-2-pyrimidinyloxy)-3-chlorophenyl]-N'-(2-glycylamino)-benzoylurea trifluoroacetate having a melting point of 212°–245° C. (decomposition).

(3) 1.37 g of the above prepared N-[4-(5-bromo-2-pyrimidinyloxy)-3chlorophenyl]-N'-(2glycylamino)-benzoylurea trifluoroacetate was dissolved in 3 ml of N,N-dimethylformamide and 2 ml of methanol, and a large excess amount of hydrochloric acid gas was introduced to the mixture under cooling with ice and stirring. When stirring could not be continued in a short time due to the precipitation of a crystal, 10 ml of methanol was added thereto and hydrochloric acid was introduced to the mixture under stirring. After completing the reaction, a crystal was collected by filtration and washed with methanol. The product thus obtained was dried in vacuo to obtain 1.08 g of the aimed product (the following compound No. 1) having a melting point of 201°–203° C.

Typical examples of a substituted benzoylurea type compound of the formula (II) used as a starting material for preparing the compound of the present invention are listed in the following Table 1.

TABLE 1

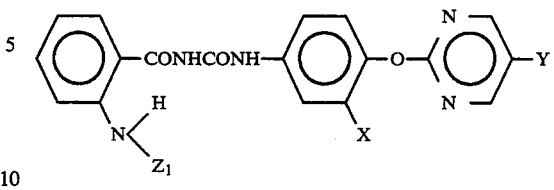

(II-1)

| X | Y | $Z_1$ | Melting point (°C.) |
|---|---|---|---|
| $C_2H_5$ | Cl | H | 195–197 |
| $C_2H_5$ | Br | H | 197–200 |
| $CH_3$ | Br | H | 189–193 |
| $CF_3$ | Cl | H | 177–182 |
| $CH_3$ | Cl | H | 176–179 |
| Cl | Br | H | 196–200 |
| Cl | Cl | H | — |

Typical examples of an intermediate compound of the formula (III) Prepared in accordance with the above Preparation Example 2 (1) are listed in the following Table 2.

TABLE 2

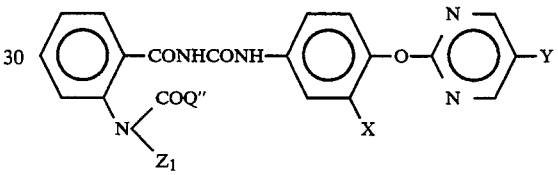

(III-1)

| Q'' | X | Y | $Z_1$ | Melting point (°C.) |
|---|---|---|---|---|
| —$CH_2NH$—Boc | Cl | Br | H | 145–192 |
| —$CH(CH_3)NH$—Boc[a) | Cl | Br | H | 140–143 |
| —CHNH—Boc[a) with $(CH_2)_2SCH_3$ | Cl | Br | H | 130–134 |
| pyrrolidine-N-Boc [a) | Cl | Br | H | (Amorphous) |
| —$CH_2NH$—Boc | $CH_3$ | Br | H | 189–191.5 |
| —$CH_2NHCOCH_2NH$—Boc | Cl | Br | H | 181–183 |
| —$CH(CH_3)NH$—Boc[b) | Cl | Br | H | (Amorphous) |
| —$CH_2NH$—Boc | $CF_3$ | Cl | H | — |
| —$CH_2NH$—Boc | Cl | Cl | H | — |
| —$CH_2NH$—Boc | Cl | Br | $CH_3$ | — |
| —$CH_2NH$—Boc | Cl | Br | $C_2H_5$ | — |
| —$CH_2NH$—Boc | $C_2H_5$ | Cl | H | — |
| —$CH_2NCH_3$—Boc | $CH_3$ | Br | H | 183–184 |
| —$CH(CH_3)NH$—Boc[a) | $CH_3$ | Br | H | 207–211 |
| —$CH(CH_3)NH$—Boc[b) | $CH_3$ | Br | H | 202–205 |

Boc: tert-butylcarbonyl group
[a)Synthesized by using a L-amino acid as a starting material.
[b)Synthesized by using a D-amino acid as a starting material.

Typical examples of a trifluoroacetate of a substituted benzoylurea derivative of the formula (I) prepared in accordance with the above Preparation Example 2 (2) are listed in the following Table 3.

TABLE 3

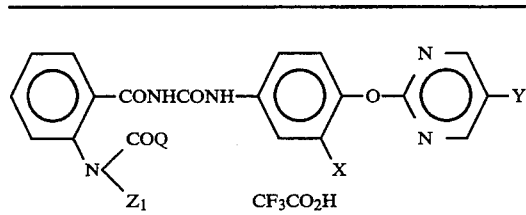

(I-1)

CF$_3$CO$_2$H

| Q | X | Y | $Z_1$ | Melting point (°C.) |
|---|---|---|---|---|
| —CH$_2$NH$_2$ | Cl | Br | H | 212–245 (Decomposition) |
| —CH(CH$_3$)NH$_2$[a)] | Cl | Br | H | 175–185 |
| (CH$_2$)$_2$SCH$_3$<br>\|<br>—CHNH$_2$ [a)] | Cl | Br | H | 130–140 |
| 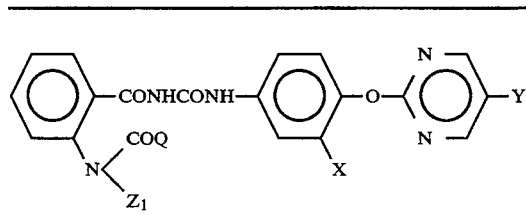 [a)] | Cl | Br | H | — |
| —CH$_2$NH$_2$ | CH$_3$ | Br | H | 207–228 |
| —CH$_2$NHCOCH$_2$NH$_2$ | Cl | Br | H | 140–145 |
| —CH(CH$_3$)NH$_2$[b)] | Cl | Br | H | (Decomposition) |
| —CH$_2$NH$_2$ | CF$_3$ | Cl | H | 198–215 |
| —CH$_2$NH$_2$ | Cl | Cl | H | 207–249 |
| —CH$_2$NH$_2$ | Cl | Br | CH$_3$ | — |
| —CH$_2$NH$_2$ | Cl | Br | C$_2$H$_5$ | — |
| —CH$_2$NH$_2$ | C$_2$H$_5$ | Cl | H | — |
| —CH$_2$NHCH$_3$ | CH$_3$ | Br | H | 186–187 |
| —CH(CH$_3$)NH$_2$[a)] | CH$_3$ | Br | H | 172–178 |
| —CH(CH$_3$)NH$_2$[b)] | CH$_3$ | Br | H | 166–170 |

[a)]Synthesized by using a L-amino acid as a starting material.
[b)]Synthesized by using a D-amino acid as a starting material.

Also, typical examples of a substituted benzoylurea derivative or its salt of the present invention are listed in the following Tables 4, 5 and 6.

TABLE 4

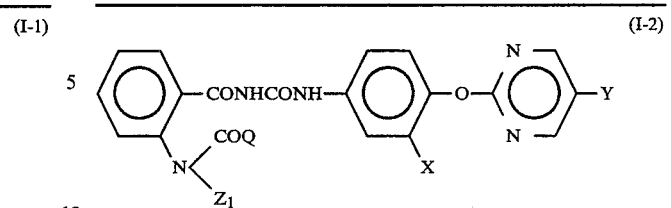

(I-2)

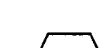

| Compound No. | Q | X | Y | $Z_1$ | Melting point (°C.) |
|---|---|---|---|---|---|
| 1 | —CH$_2$NH$_2$.HCl | Cl | Br | H | 201–203 |
| 2 | —CH$_2$N(CH$_3$)$_2$.HCl | Cl | Br | H | 164–169 |
| 3 | —CH(CH$_3$)NH$_2$.HCl[a)] | Cl | Br | H | 210–240 (Decomposition) |
| 4 | —CH(CH$_3$)NH$_2$.HCl[b)] | Cl | Br | H | 224– (Decomposition) |
| 5 | (CH$_2$)$_2$SCH$_3$<br>\|<br>—CHNH$_2$.HCl[a)] | Cl | Br | H | 170–177 |
| 6 | —CH$_2$NH$_2$.HCl | CF$_3$ | Cl | H | 184–190 |
| 7 | —CH$_2$NH$_2$.HCl | CH$_3$ | Br | H | 187–192 |

TABLE 4-continued (I-2)

| Compound No. | Q | X | Y | $Z_1$ | Melting point (°C.) |
|---|---|---|---|---|---|
| 8 | —CH$_2$NHCOCH$_2$NH$_2$.HCl | Cl | Br | H | 255–263 |
| 9 | —CH$_2$NH$_2$.HCl | Cl | Cl | H | 196–199 |
| 10 | ![pyrrolidine] [a)]<br>H.HCl | Cl | Br | H | 158–171 |
| 11 | —CH$_2$N(CH$_3$)$_3$ I$^{\ominus}$ | Cl | Br | H | 178–184 |
| 12 | —CH$_2$NH$_2$.HCl | Cl | Br | CH$_3$ | — |
| 13 | —CH$_2$N(CH$_3$)$_2$.HCl | Cl | Br | CH$_3$ | — |
| 14 | —CH$_2$NH$_2$.HCl | Cl | Br | C$_2$H$_5$ | — |
| 15 | —CH$_2$N(CH$_3$)$_2$.HCl | Cl | Br | C$_2$H$_5$ | — |
| 16 | —CH$_2$NH$_2$.HCl | C$_2$H$_5$ | Cl | H | — |

[a)]Synthesized by using a L-amino acid as a starting material.
[b)]Synthesized by using a D-amino acid as a starting material.

TABLE 5

| Compound No. | Q | X | Y | $Z_1$ | Melting point (°C.) |
|---|---|---|---|---|---|
| 17 | —CH$_2$N(CH$_3$)$_2$.HCl | C$_2$H$_5$ | Cl | H | — |
| 18 | —CH$_2$NH$_2$.HCl | C$_2$H$_5$ | Br | H | — |
| 19 | —CH$_2$N(CH$_3$)$_2$.HCl | C$_2$H$_5$ | Br | H | — |
| 20 | —CH$_2$N(CH$_3$)$_2$.HCl | CH$_3$ | Br | H | 119–132 |
| 21 | —CH$_2$N(CH$_3$)$_2$.HCl | CF$_3$ | Cl | H | — |
| 22 | —CH$_2$NH$_2$.HCl | CH$_3$ | Cl | H | — |
| 23 | —CH$_2$N(CH$_3$)$_2$.HCl | CH$_3$ | Cl | H | — |
| 24 | —CH$_2$NH$_2$.HCl | CF$_3$ | Br | H | — |
| 25 | —CH$_2$N(CH$_3$)$_2$.HCl | CF$_3$ | Br | H | — |
| 26 | CH$_2$CH(CH$_3$)$_2$<br>\|<br>—CHNH$_2$.HCl | Cl | Br | H | — |
| 27 | CH(CH$_3$)C$_2$H$_5$<br>\|<br>—CHNH$_2$.HCl | Cl | Br | H | — |
| 28 | CH(CH$_3$)$_2$<br>\|<br>—CHNH$_2$.HCl | Cl | Br | H | — |
| 29 | CH$_2$—C$_6$H$_5$<br>\|<br>—CHNH$_2$.HCl | Cl | Br | H | — |
| 30 | —CH$_2$NH$_2$.lactic acid | Cl | Br | H | — |
| 31 | —CH$_2$N(CH$_3$)$_2$.lactic acid | Cl | Br | H | - |
| 32 | —CH$_2$NH$_2$.citric acid | Cl | Br | H | — |
| 33 | —CH$_2$N(CH$_3$)$_2$.citric acid | Cl | Br | H | — |
| 34 | —CH$_2$NH$_2$.HBr | Cl | Br | H | — |

TABLE 6

| Compound No. | Q | X | Y | $Z_1$ | Melting point (°C.) |
|---|---|---|---|---|---|
| 35 | —CH$_2$N(CH$_3$)$_2$.HBr | Cl | Br | H | — |
| 36 | —CH$_2$NH$_2$.½ tartaric acid | Cl | Br | H | — |
| 37 | —CH$_2$N(CH$_3$)$_2$.½ tartaric acid | Cl | Br | H | — |
| 38 | —CH$_2$NH$_2$.HNO$_3$ | Cl | Br | H | — |
| 39 | —CH$_2$N(CH$_3$)$_2$.HNO$_3$ | Cl | Br | H | — |
| 40 | —CH$_2$NH$_2$.maleic acid | Cl | Br | H | — |
| 41 | —CH$_2$N(CH$_3$)$_2$.maleic acid | Cl | Br | H | — |
| 42 | —CH$_2$NH$_2$.½ H$_2$SO$_4$ | Cl | Br | H | — |
| 43 | —CH$_2$N(CH$_3$)$_2$.½ H$_2$SO$_4$ | Cl | Br | H | — |
| 44 | —CH$_2$NH$_2$.H$_3$PO$_4$ | Cl | Br | H | — |
| 45 | —CH$_2$N(CH$_3$)$_2$.H$_3$PO$_4$ | Cl | Br | H | — |
| 46 | —CH$_2$NH$_2$.CH$_3$SO$_3$H | Cl | Br | H | — |
| 47 | —CH$_2$N(CH$_3$)$_2$.CH$_3$SO$_3$H | Cl | Br | H | — |
| 48 | —CH$_2$N(CH$_3$)$_2$ | Cl | Br | H | 192–193 |
| 49 | —CH(CH$_3$)NH$_2$.HCl[a] | CH$_3$ | Br | H | 195–200 |
| 50 | —CH(CH$_3$)NH$_2$.HCl | CH$_3$ | Cl | H | — |
| 51 | —CH$_2$CH$_2$NH$_2$.HCl | Cl | Br | H | — |
| 52 | —CH$_2$CH$_2$CH$_2$NH$_2$.HCl | Cl | Br | H | — |
| 53 | —CH$_2$NHCH$_3$.HCl | CH$_3$ | Br | H | 194–197 (Decomposition) |
| 54 | —CH$_2$N(CH$_3$)$_2$ | CH$_3$ | Br | H | 186–192 |
| 55 | —CH(CH$_3$)NH$_2$HCl[b] | CH$_3$ | Br | H | >300 |

[a]Synthesized by using a L-amino acid as a starting material.
[b]Synthesized by using a D-amino acid as a starting material.

Compound No. 56: N-[3-(5-bromo-2-pyrimidinyloxy)-4-methylphenyl]-N'-(2-glycylamino)benzoylurea hydrochloride Compound No. 3: $[\alpha]_{589}^{20} = -11.4°$ (c 2.01, DMSO)

Compound No. 4: $[\alpha]_{589}^{20} = +14.3°$ (c 2.165, DMSO)

The compounds of the present invention are effective against experimental murine tumors such as P-388 leukemia, L-1210 leukemia, B-16 melanoma, M-5076 sarcoma, Colon 38, Colon 26 and Lewis lung carcinoma. On the other hand, certain in vivo test systems and protocols have been developed by National Cancer Institute for testing compounds to determine the effectiveness of test compounds as antineoplastic agents. These have been reported in "Cancer Chemotherapy Reports", Part III, Vol. 3, No. 2 (1972) written by Deran, Greenberg, MacDonald, Schumacher and Abott. P-388 leukemia is the most standard experimental murine tumor, and it is known that many of drugs effective against human tumor are also effective against this leukemia. Generally, the effectiveness of a drug for these experimental murine tumors is evaluated by the extended median survival time of a test mouse group to which a test drug is administered on the basis of the median survival time of a control mouse group to which no drug is administered. If the extended median survival time is at least 25–30% longer, the administered drug is determined to be effective.

Now, the antitumor activity, solubility in an aqueous solvent, doses and methods of administration of the compounds of the formula (I) will be described.

(1) Antitumor activity

Test Example 1

$1 \times 10^6$ of P-388 leukemia cells per mouse were intraperitoneally transplanted into BDF$_1$ mouse. Each formulation was intraperitoneally or intravenously administered on the 1st, 5th and 9th days after the transplantation.

The mortality was observed for 50 days. The increase life span of each group was determined by comparing the median survival time (days) of a test group to which a test drug is administered and the median survival time (days) of a control group to which physiological saline was administered at the same part as in the case of the test group. The results are shown in Table 7. Among the tested drug formulations, the compounds of the present invention were formulated in accordance with the below-mentioned Formulation Example 1, and the comparative compounds as shown in Table 8 were formulated in accordance with the below-mentioned Formulation Example 2.

(Note) * Increase life span is calculated by the following equation:

Increase life span % (ILS)=(a/b×100)−100 a: Median survival days of test group of drug administration b: Median survival days of control group of physiological saline administration (2) Solubility in water-soluble solvent

Test Example 2

About 2 mg of each of the compounds of the present invention shown in the following Table 7 was accurately weighed, and was completely dissolved in 2 ml of N,N-dimethylacetamide. The content was then transferred into a 10 ml-measuring flask, and its volume was made constant with acetonitrile. 3 ml of the resultant solution was placed in a 50 ml-measuring flask, and its volume was adjusted constant with acetonitrile to prepare a standard solution. Next, about 2 mg of each of the compounds of the present invention was weighed, and was placed in an agate mortar. Thereafter, 1.5 ml of a test liquid (water-soluble solvent) was added thereto, and the content was mixed for 5 minutes. A suspension thus obtained, was transferred into a 1.5 ml-microtube, and was centrifuged at 15,000 r.p.m. for 10 minutes. The supernatant fluid was placed in a 1 ml-microtube, and was centrifuged again under the same conditions. 0.1 ml of the supernatant fluid thus obtained was diluted with 0.9 ml of acetonitrile to prepare a measuring liquid. The above standard solution and the measuring liquid were analyzed by high pressure liquid chromatography (HPLC), and their solubilities were measured by absolute calibration curve method. The results are shown in Table 7. The amounts of the compounds of the present invention were appropriately increased or decreased depending on their solubilities.

Analyzing conditions
Column: Nucleosil 5 $C_{18}$, diameter=4.6 mm, length=250 mm
Mobile phase: acetonitrile/water/acetic acid=60/40/0.1
Detection: UV 265 nm, Column temperature: 40° C.,
Flow rate: 1.0/min
Sensitivity: 0.005 AUFS or 0.16 AUFS,
Injection volume: 20 μl

TABLE 7

Antitumour activity against P388 leukemia and solubility of Comparative Compounds and Compounds of the present invention

| Test compounds | Administered route | Increase life span (ILS %) Dose (mg/kg) | | | Solubility (ppm) Test solution | | |
|---|---|---|---|---|---|---|---|
| | | 25 | 12.5 | 6.25 | A | B | C |
| Comparative compounds | | | | | | | |
| No. 1 | ip[a] | Tox | 107 | 50 | <0.05 | 0.06 | <0.05 |
| No. 2 | ip | 148 | 83 | 34 | 0.8 | — | — |
| No. 3 | ip | 99 | 26 | 26 | <0.1 | — | — |
| No. 4 | ip | Tox | Tox | 71 | 0.4 | — | — |
| Compounds of the present invention | | | | | | | |
| No. 1 | iv[b] | 219 | 79 | 12 | 1200 | 50 | 2100 |
| No. 2 | iv | 143 | 51 | 24 | 2500 | 550 | >4000 |
| No. 3 | iv | 134 | 70 | 10 | 2800 | 320 | 3700 |
| No. 4 | iv | 95 | 19 | — | 2000 | 140 | 2700 |
| No. 5 | iv | 152 | 3 | — | 1200 | 30 | 2000 |
| No. 6 | iv | — | 138 | 60 | 1400 | 70 | 1900 |
| No. 7 | iv | 143 | 105 | 50 | >2300 | 380 | 3900 |
| No. 8 | iv | 243 | 90 | — | 1800 | 70 | 2100 |
| No. 9 | iv | 152 | 86 | 19 | 1600 | 160 | 1500 |
| No. 20 | iv | 155 | 36 | — | 19000 | 3000 | 20000 |
| No. 49 | iv | 190 | 76 | 14 | 7600 | 1800 | 9800 |
| No. 53 | iv | >50[c] | >30[d] | — | 5000 | 120 | — |

[a]Intraperitoneally
[b]Intravenously
[c]20 mg/kg
[d]10 mg/kg
Test solutions used are as follows:
Test solution A: Distilled water
Test solution B: Physiological saline
Test solution C: 10% polyethylene glycol #400 aqueous solution

TABLE 8

<chemical structure: phenyl(NH2)-CONHCONH-phenyl(X')-O-pyrimidinyl-Y'>

| Comparative compound No. | X' | Y' |
|---|---|---|
| 1 | Cl | Br |
| 2 | $CH_3$ | Cl |
| 3 | $C_2H_5$ | Br |
| 4 | $CF_3$ | Cl |

(3) Acute toxicity

None of $BDF_1$ mice were dead by intravenously administering each formulation of Compound Nos. 1 to 9, 20, 49 and 53 of the present invention prepared in accordance with Formulation Example 1 in an amount of 25 mg/kg mouse (on the basis of compound). Thus, it was recognized that the acute toxicity value (LD 50) of Compound Nos. 1 to 9, 20, 49 and 53 was at least 25 mg/kg.

(4) Dose and method for administration

As the method for administration, in the case of animals, drugs may be administered by injection such as intraperitoneal injection, intravenous injection or local administration, or by oral administration. In the case of human being, drugs may be administered by injection such as intravascular injection to a vein or an arteria or local administration, by oral administration, or as a suppository. The dose is determined in view of the results of animal experiments and various conditions within a range that the total amount does not exceed a certain amount. Drugs may be administered continuously or intermittently. However, the dose may optionally vary depending upon the method for administration, the patient or the condition of an animal to be treated such as age, body weight, sex, sensitivity, food, time of administration, drugs used together or degree of the patient or the disease. The suitable amount and the numbers of administration under a certain condition, must be determined by the determination test of a suitable amount by a specialist based on the above guidelines.

The antitumor agent of the present invention may be formulated in the same manner as in the case of usual drugs. It is formulated from the active ingredient and various pharmaceutically acceptable adjutants such as an inert diluent. The formulation can be administered orally or intravenously, or in the form of a suppository.

Further, the content of the active ingredient in the antitumor agent of the present invention varies depending upon the difference of various conditions and can not generally be defined. The agent may contain the active ingredient in the same manner as in the case of usual antitumor agents. For example, it may contain at least 0.01% of the active ingredient.

Now, specific Formulation Examples of the antitumor agent of the present invention will be mentioned.

Formulation Example 1

0.125 part by weight of the above mentioned Compound No. 1 was dissolved in 5 parts by weight of N,N- dimethylacetamide and 5 parts by weight of polyoxyethylene sorbitan monooleate, and 90 parts by weight of physiological saline was added thereto to form a solution formulation in an agate mortar.

Formulation Example 2

0.125 part by weight of Comparative Compound No. 1 was dissolved in 5 parts by weight of N,N-dimethylacetamide and 5 parts by weight of polyoxyethylene sorbitan monooleate, and 90 parts by weight of physiological saline was added thereto to form a suspension formulation in an agate mortar.

Formulation Example 3

1 part by weight of the above-mentioned Compound No. 1 was dissolved in 100 parts by weight of polyethylene glycol #400 to form a uniform solution formulation.

Formulation Example 4

1 part by weight of the above-mentioned Compound No. 2 was dissolved in 50 parts by weight of polyethylene glycol #400 to form a uniform solution, and the resultant solution was added to 5,000 parts by weight of physiological saline to form a solution formulation.

Formulation Example 5

1 part by weight of the above-mentioned Compound No. 1 was dissolved in 50 parts by weight of polyethylene glycol #400 to form a uniform solution, and the resultant solution was added to 5,000 parts by weight of a 5% glucose solution to form a solution formulation.

Formulation Example 6

1 part by weight of the above-mentioned Compound No. 2 was dissolved in 5,000 parts by weight of physiological saline to form a uniform solution formulation.

Formulation Example 7

1 part by weight of the above-mentioned Compound No. 7 was dissolved in 5,000 parts by weight of a 5% glucose solution to form a uniform solution formulation.

According to the present invention, the novel substituted benzoylurea derivative of the formula (I) or its salt exhibits a satisfactory antitumor activity against mammal tumors such as leukemia, melanoma, sarcoma and carcinoma, and since its water-solubility is satisfactorily high, this compound provides an improved pplicability as an antitumor agent.

We claim:

1. A substituted benzoylurea having the formula (I), or its salt;

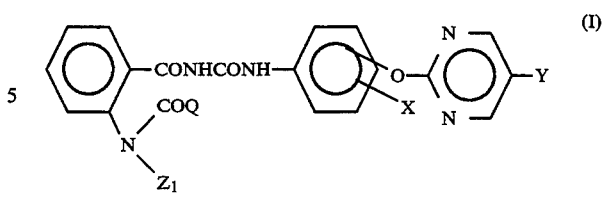

wherein Q is a $-R_1N(Z_2)Z_3$ group or a $-R_2N(Z_4)COR_1N(Z_2)Z_3$ group; and $R_1$ and $R_2$ are respectively an alkanediyl group which may be substituted with a lower alkylthio group or a phenyl group; $Z_1$, $Z_2$, $Z_3$ and $Z_4$ are respectively a hydrogen atom or a lower alkyl group; $R_1$ and $R_2$ may be bonded with each other to form a morpholino, aziridinyl, pyrrolidinyl, piperidino or pyrrolyl ring with an adjacent nitrogen atom; X is a halogen atom, a lower alkyl group or a trifluoromethyl group; and Y is a halogen atom.

2. The compound or its salt, according to claim 1, wherein $Z_1$ is a hydrogen atom.

3. The compound or its salt, according to claim 2, wherein Q is a $-R_1N(Z_2)Z_3$ group (in which $R_1$ is an alkanediyl group and $Z_2$ and $Z_3$ are respectively a hydrogen atom or a lower alkyl group).

4. The compound or its salt, according to claim 2, wherein X is a chlorine atom or a methyl group and Y is a chlorine atom or a bromine atom.

5. The compound or its salt, according to claim 2, wherein the substituted benzoylurea derivative is N-[4-(5-bromo-2-pyrimidinyloxy)-3-methylphenyl]-N'-(2-glycylamino)benzoylurea; N-[4-(5-bromo-2-pyrimidinyloxy)-3-methylphenyl]-N'-[2-(N,N-dimethylglycyl)amino]benzoylurea; N-[4-(5-bromo-2-pyrimidinyloxy)-3-methylphenyl]-N'-(2-sarcosylamino)benzoylurea; or their salts.

6. A compound having the formula (III),

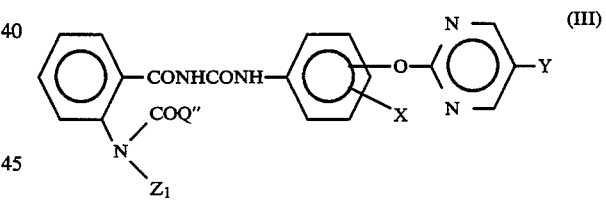

wherein Q" is a $-R_1N(Z_2)A'$ group or a $R_2N(Z_4)COR_1N(Z_2)A'$ group; $R_1$ and $R_2$ are respectively an alkanediyl group which may be substituted with a lower alkylthio group or a phenyl group; $Z_1$, $Z_2$, $Z_3$ and $Z_4$ are respectively a hydrogen atom or a lower alkyl group; $R_1$ and $Z_2$ may be bonded with each other to form a morpholino, aziridinyl, pyrrolidinyl, piperidino or pyrrolyl ring with an adjacent nitrogen atom; A' is a benzyloxycarbonyl, tert-butyloxycarbonyl, p-biphenylisopropyloxycarbonyl, formyl, 2-nitrophenylsulfenyl or diphenylphosphinothiolyl protective group; X is a halogen atom, a lower alkyl group or a trifluoromethyl group, and Y is a halogen atom.

* * * * *